(12) United States Patent
Little et al.

(10) Patent No.: US 11,529,280 B2
(45) Date of Patent: Dec. 20, 2022

(54) EXOSKELETON AND MOUNTING ARRANGEMENT

(71) Applicant: Rex Bionics Pty Ltd., Melbourne (AU)

(72) Inventors: Richard Little, Torbay (NZ); Jehangir Dinyar Shishbaradaran, Golflands (NZ)

(73) Assignee: Rex Bionics Limited, Auckland (NZ)

( * ) Notice: Subject to any disclaimer, the term of this patent is extended or adjusted under 35 U.S.C. 154(b) by 0 days.

(21) Appl. No.: 16/227,452

(22) Filed: Dec. 20, 2018

(65) Prior Publication Data

US 2019/0192372 A1 Jun. 27, 2019

(30) Foreign Application Priority Data

Dec. 21, 2017 (AU) ................................ 2017905136

(51) Int. Cl.
  *A61H 3/00* (2006.01)
  *A61H 1/02* (2006.01)
  *A61F 2/60* (2006.01)
  *A61F 2/80* (2006.01)

(52) U.S. Cl.
  CPC ............... *A61H 3/00* (2013.01); *A61F 2/60* (2013.01); *A61F 2/80* (2013.01); *A61H 1/024* (2013.01);
  (Continued)

(58) Field of Classification Search
  CPC ........ A61H 3/00; A61H 1/0237; A61H 1/024; A61H 1/0244; A61H 1/0262;
  (Continued)

(56) References Cited

U.S. PATENT DOCUMENTS

| 2011/0066088 A1* | 3/2011 | Little | A61H 1/0255 |
| | | | 601/35 |
| 2012/0004736 A1* | 1/2012 | Goldfarb | A61F 2/60 |
| | | | 623/25 |

(Continued)

FOREIGN PATENT DOCUMENTS

| WO | WO 2009/082249 | 7/2009 |
| WO | WO 2011/002306 | 1/2011 |

(Continued)

OTHER PUBLICATIONS

European Search Report, Application No. 18213720.8-1126, dated Apr. 26, 2019, pp. 1-9.

*Primary Examiner* — Jerrah Edwards
*Assistant Examiner* — Aren Patel
(74) *Attorney, Agent, or Firm* — Fish & Richardson P.C.

(57) ABSTRACT

There is disclosed a mobility aid for use by a user having a lower body amputation site. The mobility aid includes a lower body exoskeleton (LBE). The LBE has a pelvic support structure and a first leg and a second leg. Each of the first and second legs are movably coupled to the pelvic support structure, wherein at least the first and second legs are selectively actuable to move the lower body exoskeleton relative to a surface on which the mobility aid is positioned. The LBE also includes a carrier selectively positionable with respect to the lower body exoskeleton and, which in use, supports the user at or about an amputation site; and a harness system configured to, when in use, secure the user to the lower body exoskeleton.

16 Claims, 12 Drawing Sheets

(52) U.S. Cl.
CPC .......... *A61H 1/0237* (2013.01); *A61H 1/0244* (2013.01); *A61H 1/0262* (2013.01); *A61H 1/0266* (2013.01); *A61H 2003/005* (2013.01); *A61H 2003/007* (2013.01); *A61H 2201/0192* (2013.01); *A61H 2201/1215* (2013.01); *A61H 2201/149* (2013.01); *A61H 2201/163* (2013.01); *A61H 2201/164* (2013.01); *A61H 2201/165* (2013.01); *A61H 2201/1628* (2013.01); *A61H 2201/1633* (2013.01); *A61H 2201/1642* (2013.01); *A61H 2201/1647* (2013.01); *A61H 2201/1676* (2013.01); *A61H 2201/501* (2013.01); *A61H 2201/5035* (2013.01); *A61H 2201/5046* (2013.01); *A61H 2201/5061* (2013.01); *A61H 2201/5064* (2013.01); *A61H 2201/5097* (2013.01); *A61H 2205/10* (2013.01); *A61H 2230/855* (2013.01)

(58) Field of Classification Search
CPC ............ A61H 1/0266; A61H 2003/005; A61H 2003/007; A61H 2201/0192; A61H 2201/1215; A61H 2201/149; A61H 2201/1628; A61H 2201/163; A61H 2201/1633; A61H 2201/165; A61F 2/60; A61F 2/80

USPC .......................................................... 623/25

See application file for complete search history.

(56) References Cited

U.S. PATENT DOCUMENTS

| | | | | |
|---|---|---|---|---|
| 2012/0259432 | A1* | 10/2012 | Dillingham | A61F 2/76 623/31 |
| 2014/0195009 | A1* | 7/2014 | Green | A61F 2/66 623/38 |
| 2014/0277581 | A1* | 9/2014 | Steele | A61F 2/70 623/24 |
| 2015/0127119 | A1* | 5/2015 | Simon | A61F 2/72 623/25 |
| 2015/0190248 | A1* | 7/2015 | Vitiello | A61F 2/60 623/24 |
| 2016/0158029 | A1 | 6/2016 | Kuiken et al. | |

FOREIGN PATENT DOCUMENTS

| | | |
|---|---|---|
| WO | WO 2013/190495 | 12/2013 |
| WO | WO 2015/080596 | 6/2015 |

* cited by examiner

16
EXOSKELETON AND MOUNTING ARRANGEMENT

FIELD OF THE INVENTION

The present invention relates to a mobility aid for use by an amputee. In an exemplary form it relates to a robotic exoskeleton that can effect exercise, rehabilitation, and physical therapy movements including walking and standing.

BACKGROUND OF THE INVENTION

Mobility aids in the form of robotic exoskeletons are known for fully or partially supporting and assisting a disabled user. Examples of robotic exoskeletons are described in the applicant's earlier PCT publications, WO 2015/080596, WO 2009/082249, and WO 2011/002306, each of which is hereby incorporated by reference.

FIG. 1 shows a lower body robotic exoskeleton 500 (using reference numbers corresponding to WO 2015/080596). The exoskeleton 500 may be configured as a fully supportive system to assist a paraplegic user for example, or may be configured as a partially or fully supportive system to assist in the rehabilitation of a user 200 with limited mobility. The exoskeleton 500 is an electromechanical skeletal structure worn externally by the user 200 and is configured to support the legs and waist of the user.

The exoskeleton 500 comprises a pair of leg structures 510, 520 each configured to receive and retain a respective leg of the user, a pair of feet 530, 540 each configured to receive and retain a respective foot of the user, and a pelvic support structure 550 adapted to receive and retain the user's pelvis and hips. Each leg structure 510, 520 comprises an upper leg structure 511, 521 and a lower leg structure 512, 522. The upper and lower leg structures are moveably coupled relative to one another at a knee joint 513, 523 of the leg structure. Each upper leg structure 511, 521 is also moveably coupled to a respective side of the hip at a hip joint 514, 524, while each lower leg structure 512, 522 is also moveably coupled to the respective foot 530, 540 at an ankle joint 515, 525 of the leg structure. In this manner, the lower body exoskeleton 500 is capable of effecting motion to the user's lower limbs, and to the user's upper body via the hip joints 514, 524.

There is an ongoing need to improve the functionality and versatility of assistive robotic exoskeletons, such as the exoskeleton shown in FIG. 1. In particular, there is a need to improve the functionality of robotic exoskeletons for users that have one or more lower body amputations.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In an aspect, the present invention provides a mobility aid for use by a user having a lower body amputation site, the mobility aid including:
a lower body exoskeleton including:
 a pelvic support structure;
 a first leg and a second leg, each of the first and second legs movably coupled to the pelvic support structure, wherein at least the first and second legs are selectively actuable to move the lower body exoskeleton relative to a surface on which the mobility aid is positioned;
 a carrier selectively positionable with respect to the lower body exoskeleton and, which in use, supports the user at or about an amputation site; and
 a harness system configured to, when in use, secure the user to the lower body exoskeleton.

Preferably, the carrier and the harness system, in combination, cooperate to position the user, when in use, at a predetermined position relative to the lower body exoskeleton.

The first and second legs are preferably pivotally coupled to the pelvic support structure at respective first and second hip joints, each of the first and second hip joints defining respective first and second hip axes about which the legs have a rotational degree of freedom. The predetermined position preferably corresponds to at least one of said hip axes such that, when in use, at least one of the user's hips if present are located at or proximate to at least one of said first and second hip axes. If the user does not have any hips due to amputation, the user is preferably located in the predetermined position such that an imaginary hip axis of the user is located at or approximate to at least one of said first and second hip axes of the lower body exoskeleton.

The carrier may be configured to support an amputation site corresponding to a remaining part of a lower limb of the user after amputation. For example, in a first embodiment, the carrier may be configured to support a remaining part of the user's femur or upper leg. In a second embodiment, the carrier may be configured to support a remaining part of the user's tibia or fibula, or lower leg. In a third embodiment, the carrier may be configured to support an amputation site corresponding to a remaining part of a user's pelvis or hips after amputation. The carrier may be configured to support more than one amputation site simultaneously.

In some embodiments, the carrier is selectively positionable with respect to the first and second legs in any one or more of a vertical and horizontal directions in the saggital plane, and/or a pivot axis normal to the saggital plane.

In each of the embodiments mentioned above, the carrier can include a mounting arrangement for releasably mounting the carrier to the lower body exoskeleton. In a first embodiment, the carrier may be releasably mounted to one of the first and second legs such that the carrier is selectively positionable with respect to the leg to which it is mounted. Each of the first and second legs preferably include respective upper and lower leg structures. The upper and/or lower leg structure to which the carrier is mounted can include a first guide adapted to receive and retain the carrier. Preferably, the carrier comprises a first carriage portion configured to interface with the first guide such that the carrier can be selectively positioned along the first guide.

The first carriage portion is preferably slidably received by the first guide and is releasably securable to the first guide at a desired position along the first guide. The first guide is preferably elongate in overall form. The first guide can include one or more rails. In the event that the first guide is associated with the upper leg structure of the first or second leg, the first guide preferably has a longitudinal axis that is parallel, or substantially parallel, to a femoral axis of the respective leg structure. Similarly, in the event that the first guide is associated with the lower leg structure of the first or second leg, the first guide preferably has a longitudinal axis that is parallel, or substantially parallel, to a tibial axis of the respective leg structure. Accordingly therefore, the carrier is selectively positionable in a vertical direction in the saggital plane. The first guide preferably includes a stop at one end, for example, a lower end, to define a limit of sliding travel of the carrier on the first guide.

The first carriage portion preferably includes a first recess that slidingly interfaces with one or more rails of the first guide such that the carrier is slidable along the first guide. In one form, the first recess may comprise a dovetail-shaped recess and the first guide may comprise a corresponding dovetail-shaped rail that slidingly interfaces with the dovetail-shaped recess. The carrier is preferably securable along the first guide at the desired position by one or more fasteners that may, for example, be received through the first carriage portion to engage the first guide.

The carrier also preferably includes a second carriage portion and a third carriage portion. The second carriage portion is preferably laterally translatable on the first carriage portion, and the second carriage portion preferably includes a second guide that slidingly receives the third carriage portion. The second guide may comprise a dovetail-shaped recess and the third carriage portion may comprise a corresponding dovetail-shaped rail that slidingly interfaces with the dovetail-shaped recess. The third carriage portion may be slidable in the dovetail-shaped recess until it is seated against a lower surface of the first carriage portion. The dovetail-shaped recess of the second carriage portion is preferably generally perpendicular to the transverse channel of the first carriage portion. Advantageously therefore, the third carriage portion is selectively positionable in a horizontal direction in the saggital plane. Ultimately therefore, the carrier is selectively positionable in at least two perpendicular axes in the saggital plane.

The third carriage portion may be pivotably movable with respect to the second carriage portion. Preferably, the third carriage portion is pivotable about a pivot axis substantially perpendicular to a longitudinal axis extending through the transverse channel of the first carriage portion and substantially perpendicular to the longitudinal axis of the first guide. Accordingly, the third carriage portion may pivot toward anterior and posterior directions about the pivot axis, which pivot axis is normal to the saggital plane. Preferably, the third carriage portion may pivot approximately 10° in both the anterior and posterior directions. As is typical in upper leg amputations, the remaining part of the leg may have a reduced range of motion or may have a generally forward resting position. Therefore, advantageously, the pivotable movement of the third carriage portion may allow for a more comfortable securement of the remaining part of the user's upper leg to the lower body exoskeleton.

The carrier can comprise a coupling to couple the carrier with a prosthetic. In an embodiment the third carriage portion can includes the coupling to couple the carrier with a prosthetic. In some embodiments, the coupling comprises a component of a Ferrier coupler. Typically this will be a male Ferrier coupler configured to mate with a female Ferrier coupler of a prosthetic. The male and female Ferrier couplers preferably include alignable through-holes such that a fastener may be received though the through-holes to releasably secure the prosthetic to the third carriage portion. Although a male and female Ferrier coupling is utilised in the present embodiment, a person skilled in the art would appreciate that other couplings, preferably of a standard type, could be used to couple the carrier and the prosthetic. In one embodiment, the prosthetic may comprise a socket. The socket may be shaped like an inverted bell. The socket preferably includes, on an inner surface thereof, a seating surface configured to support the amputation site of the user. In this embodiment, the seating surface may receive and seat a stump of the user, wherein the stump corresponds to the remaining part of a lower limb of the user after amputation.

In an alternative second embodiment, the carrier may be releasably mounted to the pelvic support structure such that the carrier is selectively positionable with respect to the pelvic support structure in a vertical direction in the saggital plane. In this embodiment, the carrier may include a platform that defines a seating surface configured to support the amputation site of the user. The platform is preferably configured to support an amputation site corresponding to a remaining part of a user's pelvis or hips after amputation.

The platform is preferably dimensioned to engage an inner wall of the pelvic support structure. In one embodiment, an outer side wall of the platform may engage the inner wall of the pelvic support structure substantially along its entire length. In an alternative embodiment, the outer side wall of the platform may only engage the inner wall of the pelvic support structure partially along its length. In either embodiment, the mounting arrangement includes one or more straps which, at a first end, are respectively received in one or more first apertures spaced apart and connected to the platform at its outer side wall. A second opposite end of each of the more or more straps are respectively received in one or more second apertures associated with an upper end of the pelvic support structure. Preferably, the one or more second apertures may be located in a combined back brace and torso support structure that is releasably connected about the upper end of the pelvic support structure. The second end of each of the more or more straps are preferably respectively secured in one or more braces associated with the combined back brace and torso support. By adjusting the length of the one or more straps between the first and second apertures, the platform is selectively positionable with respect to the pelvic support structure.

The first and second legs are preferably length adjustable to suit the user. For example, the upper and lower leg structures of each of the first and second legs may include at least two leg members that are selectively positionable with respect to each other. Accordingly, both the upper leg structure and the lower leg structure of each of the first and second legs are preferably length adjustable. Advantageously therefore, embodiments of the present invention provide a double adjustability arrangement, i.e. the first and second legs are length adjustable to suit the length of the user's legs (if present), and in addition, the position of the carrier on the exoskeleton is also adjustable to suit the amputation site of the user. In the first embodiment mentioned above, the carrier is selectively positionable with respect to the first and second legs in vertical and horizontal directions in the saggital plane, and may also pivot about a pivot axis normal to the saggital plane. In the second embodiment mentioned above, the carrier is selectively positionable with respect to the pelvic support structure in a vertical direction in the saggital plane.

The harness system of the lower body exoskeleton may include braces, tethers, strapping, a harness, or webbing to hold the user's hips snugly to the pelvic support structure. The harness system may also include adjustable straps or webbing that extend about other parts of the user's body, for example, the torso and/or at least one limb or a remaining part of at least one limb of the user. The harness system may also include an orthotics system configured to interface with and secure, if present, at least one foot of the user to the lower body exoskeleton. Advantageously, the harness system and the orthotics system provides stability to the user when the user is secured to the lower body exoskeleton.

The lower body exoskeleton may include a second carrier selectively positionable with respect to the lower body exoskeleton that supports the user at or about a second amputation site. The second carrier can include all of the features of the carrier described above.

In another aspect the present invention provides a user support arrangement for a lower body exoskeleton. The user the user support arrangement may comprise:

A guide configured to be affixed to a leg of a lower body exoskeleton;

A carrier releasably mounted to the guide and positionable with respect to the guide and lower body exoskeleton, said carried being arranged in use to support a user of the lower body exoskeleton at or about an amputation site.

Such a user support arrangement for a lower body exoskeleton can be fitted to a suitable exoskeleton to enable its use by a an amputee. The carrier and guide may include any of the features of the carrier and guide arrangements set out in relation to the first aspect of the present embodiment above.

The carrier may comprise a first carriage first carriage portion is slidably received by the guide and is releasably securable to the guide at a desired position along the guide such that the carrier can be selectively positioned along the guide. The carrier can include a second carriage portion and a third carriage portion, the second carriage portion being laterally translatable on the first carriage portion, and the third carriage portion being pivotably movable with respect to the second carriage portion. The carrier can comprise a coupling to couple the carrier with a prosthetic. For example the coupling comprises a component of a Ferrier coupler.

The lower body exoskeleton may be a lower body exoskeleton as described in the applicant's earlier PCT publications, WO 2015/080596, WO 2009/082249, and WO 2011/002306.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
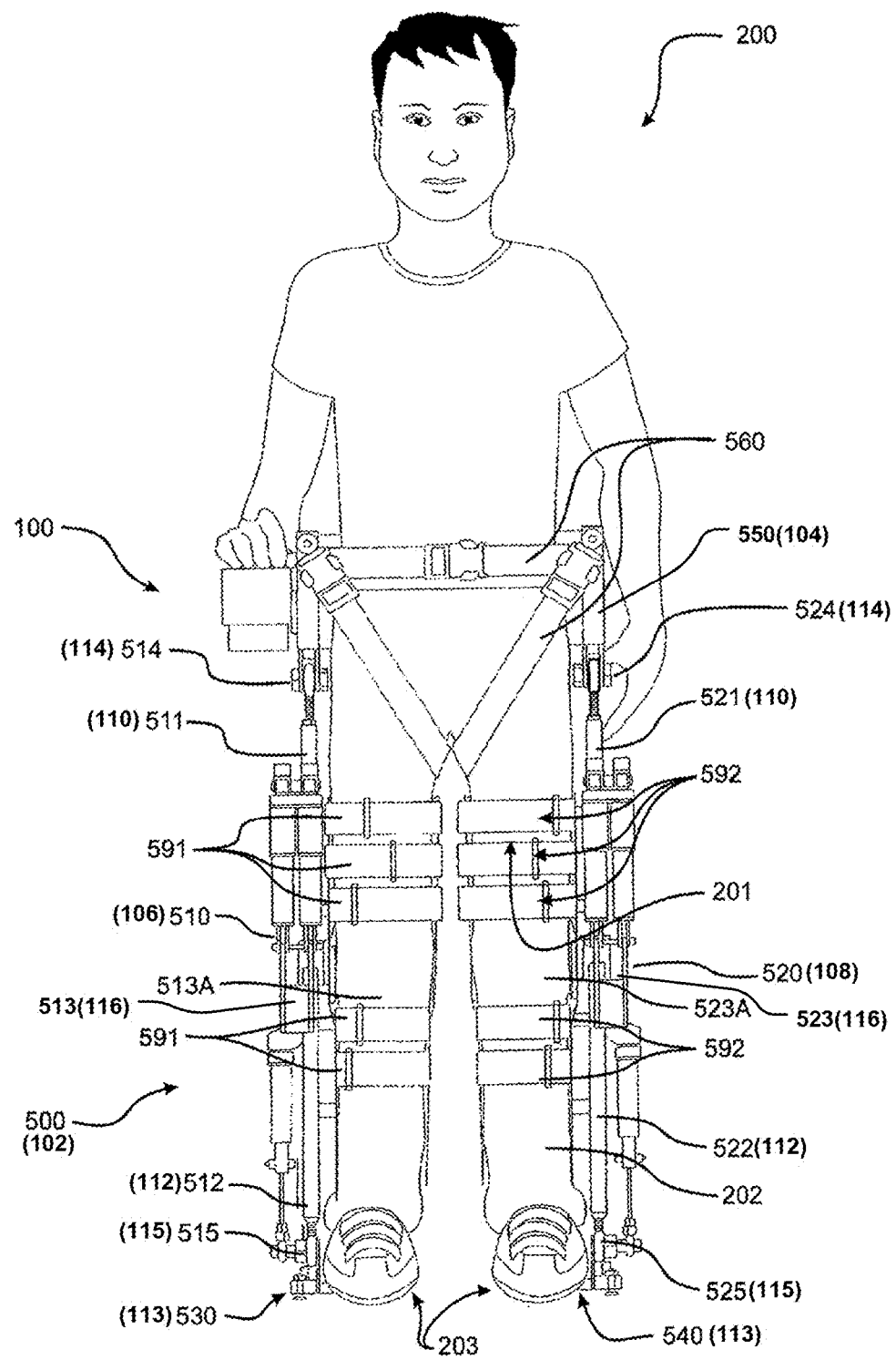
FIG. 1 is a front view of a prior art mobility aid comprising a lower body exoskeleton having a user secured thereto.
Figure 2:
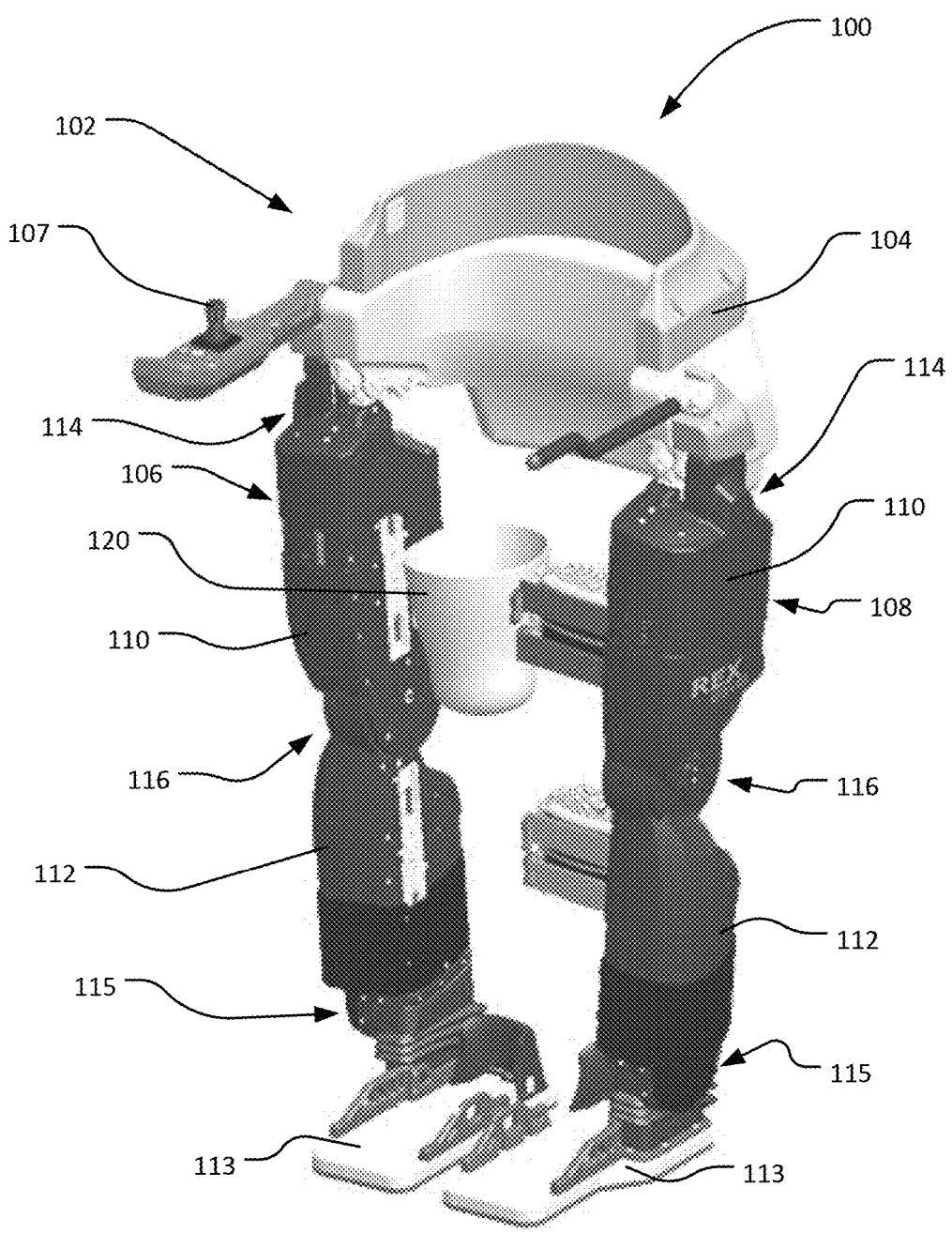
FIG. 2 is a perspective view of a mobility aid comprising a lower body exoskeleton according to an embodiment of the present invention.

Referring to FIG. 2, there is shown a mobility aid 100 according to an embodiment of the invention. Advantageously, as is described below, the mobility aid 100 may assist a user having a lower body amputation site to at least stand, walk, and perform rehabilitation movements whilst the user is secured to the mobility aid 100. The mobility aid 100 is an improvement over known existing mobility aids, such as the one shown in FIG. 1, which are not adapted to support amputees.

The mobility aid 100 comprises a lower body exoskeleton (LBE) 102 having a pelvic support structure 104 and a pair of legs 106, 108. The legs 106, 108 are movably coupled to the pelvic support structure 104 and are selectively actuable, via a user interface 107, to move the LBE 102 relative to a surface on which the mobility aid 100 is positioned. According to the invention, the LBE 102 includes a carrier 120 which is selectively positionable with respect to the LBE 102, and which in use, supports the user at or about an amputation site. The LBE 102 also includes a harness system (not shown) configured to secure the user to the LBE 102.

The pelvic support structure 104 is shaped and configured to support the user's pelvis and hips when the user is secured to the LBE 102 with the harness system. The harness system is preferably the harness system described in WO 2015/080596. Each of the legs 106, 108 include respective upper and lower leg structures 110, 112 that are configured to receive and retain a respective leg (or a remaining part of a respective leg) of the user when the user is secured to the LBE 102 with the harness system.

Each upper leg structure 110 is movably coupled to a respective lateral side of the pelvic support structure 104 at a hip joint 114. Each hip joint 114 enables relative rotation between the upper leg structure 110 and the pelvic support structure 104 about two substantially orthogonal hip axes in the manner described in the abovementioned PCT publication. Specifically, each hip joint 114 enables hip/leg flexion and hip/leg extension movements in the LBE 102 about a first hip axis, and leg abduction and leg adduction movements in the LBE 102 about a second hip axis substantially orthogonal to the first hip axis. Thus, when the user is secured to the LBE 102, each hip joint 114 enables movement of the user's legs (or a remaining part thereof) relative to the user's hips along a sagittal plane of the user in the anterior and posterior directions. Additionally, each hip joint 114 enables movement of the user's legs (or a remaining part thereof) relative to the user's hips along a coronal plane of the user in lateral and medial directions.

A lower end of the upper leg structure 110 of each leg 106, 108 is movably coupled to an upper end of the lower leg structure 112 of the same leg 106, 108 at a knee joint 116. Each knee joint 116 enables extension and flexion of the lower leg structure 112 relative to the upper leg structure 110. Thus, when the user is secured to the LBE 102, each knee joint 116 enables movement of the user's lower leg (if present) relative to the user's upper leg (if present) along the sagittal plane of the user in the anterior and posterior directions.

A lower end of the lower leg structure 112 of each leg 106, 108 is movably coupled to a foot 113 at an ankle joint 115. Each ankle joint 115 enables relative rotation between the respective lower leg structure 112 and foot 113 about two substantially orthogonal axes to achieve ankle/foot dorsiflexion movements, ankle/foot plantar flexion movements, ankle/foot inversion movements, and ankle/foot eversion movements. Each foot 113 of the LBE 102 is configured to receive and retain a respective foot (if present) of the user, and is further configured to support the LBE 102 on a surface on which the mobility aid 100 is positioned.

The LBE 102 further includes a series of actuators (not shown) to enable movement of the upper leg structure 110 of each leg 106, 108 at the hip joints 114, and to enable movement of the lower leg structure 112 of each leg 106, 108 at the knee joints 116, and to enable movement of the foot of each leg 106, 108 at the ankle joints. Each of the actuators are selectively actuable by the user, via the user interface 107, to at least move the LBE 102 relative to the surface on which the mobility aid 100 is positioned. As is mentioned above, the LBE 102 is configured to assist the user to at least stand, walk, and perform rehabilitation movements.

The manner in which the amputation site of the user is supported by the LBE 102 will now be described with reference to FIGS. 3 to 13. In a first embodiment (FIGS. 3 to 6), the LBE 102 includes a carrier 120 (FIG. 5) that is selectively positionable with respect to the upper leg structure 110. When in use, the carrier 120 is configured to support a remaining part of the user's upper leg corresponding to an above-knee amputation. Although only a first leg 106 and a single carrier 120 is illustrated in FIGS. 3 to 6, the LBE 102 may include another carrier 120 that is selectively positionable with respect to the upper leg structure 110 of the second leg 108. In other words, the LBE 102 may be configured to support a user having above-knee amputations of both legs.

Figure 3:
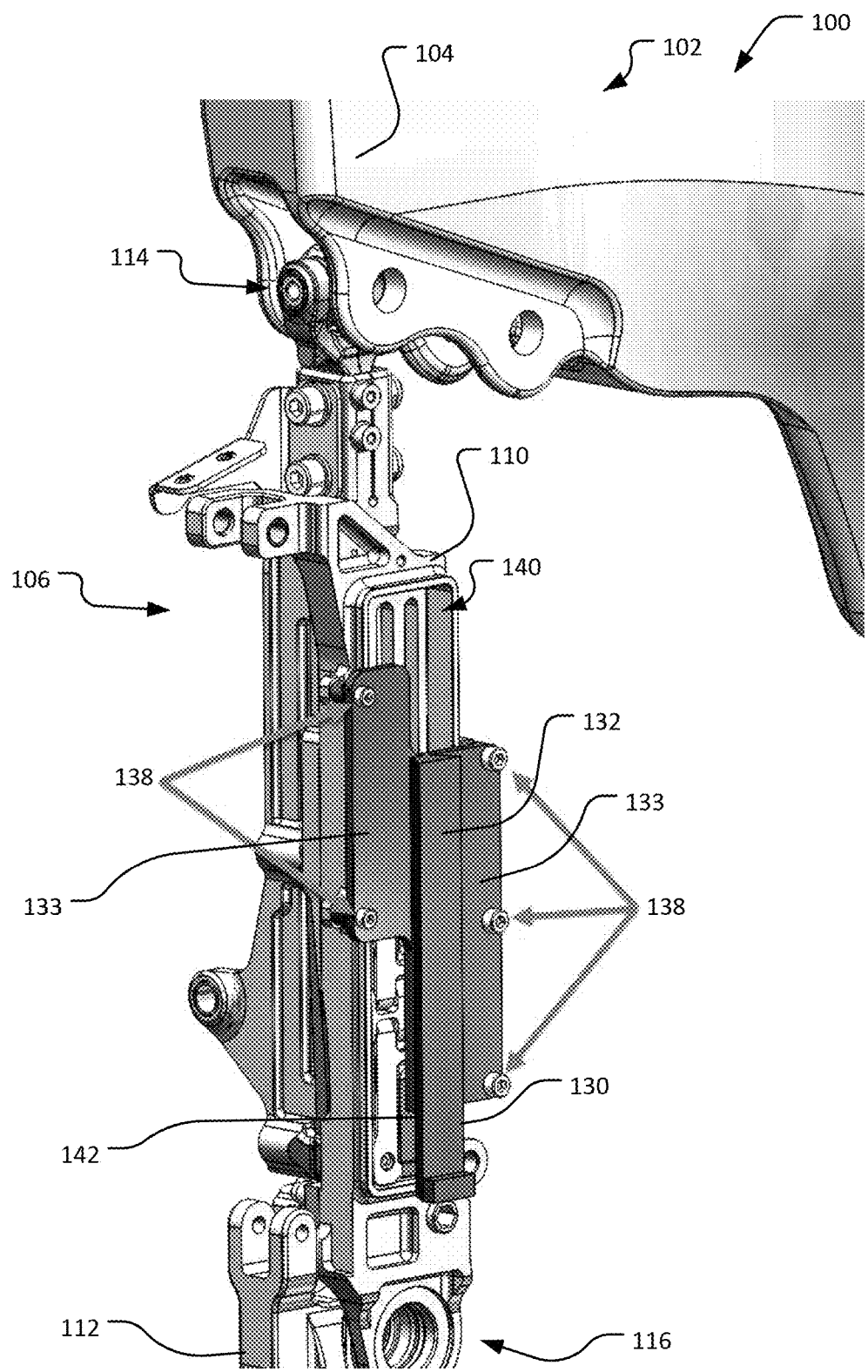
FIG. 3 is a perspective view of an upper leg structure of a single leg of the lower body exoskeleton of FIG. 2.

The carrier 120 includes a mounting arrangement for releasably mounting the carrier to the LBE 102. Referring to FIG. 3, the mounting arrangement includes a generally elongate first guide 130. The elongate first guide 130 has a central elongate rail 132 and a pair of lateral extensions 133 extending outwardly from opposite longitudinal sides of the central rail 132. Each lateral extension 133 includes at least two apertures configured to receive a fastener 138 to releasably fasten the first guide 130 to an inner side surface 140 of the upper leg structure 110 (the inner side surface 140 faces toward the non-illustrated second leg 108). The elongate first guide 130 is fastened to the upper leg structure 110 such that a longitudinal axis of the first guide 130 is parallel, or substantially parallel, to a longitudinal axis (or femoral axis) of the upper leg structure 110.

The central rail 132 of the first guide 130 is dovetail-shaped and protrudes outwardly from the inner side surface 140 of the upper leg structure 110 (toward the non-illustrated second leg 108). An outer surface of the dovetail-shaped rail 132 defines a guide surface 142 which is configured to slidably receive a first carriage portion 150 (FIG. 4) thereon.

Figure 4:
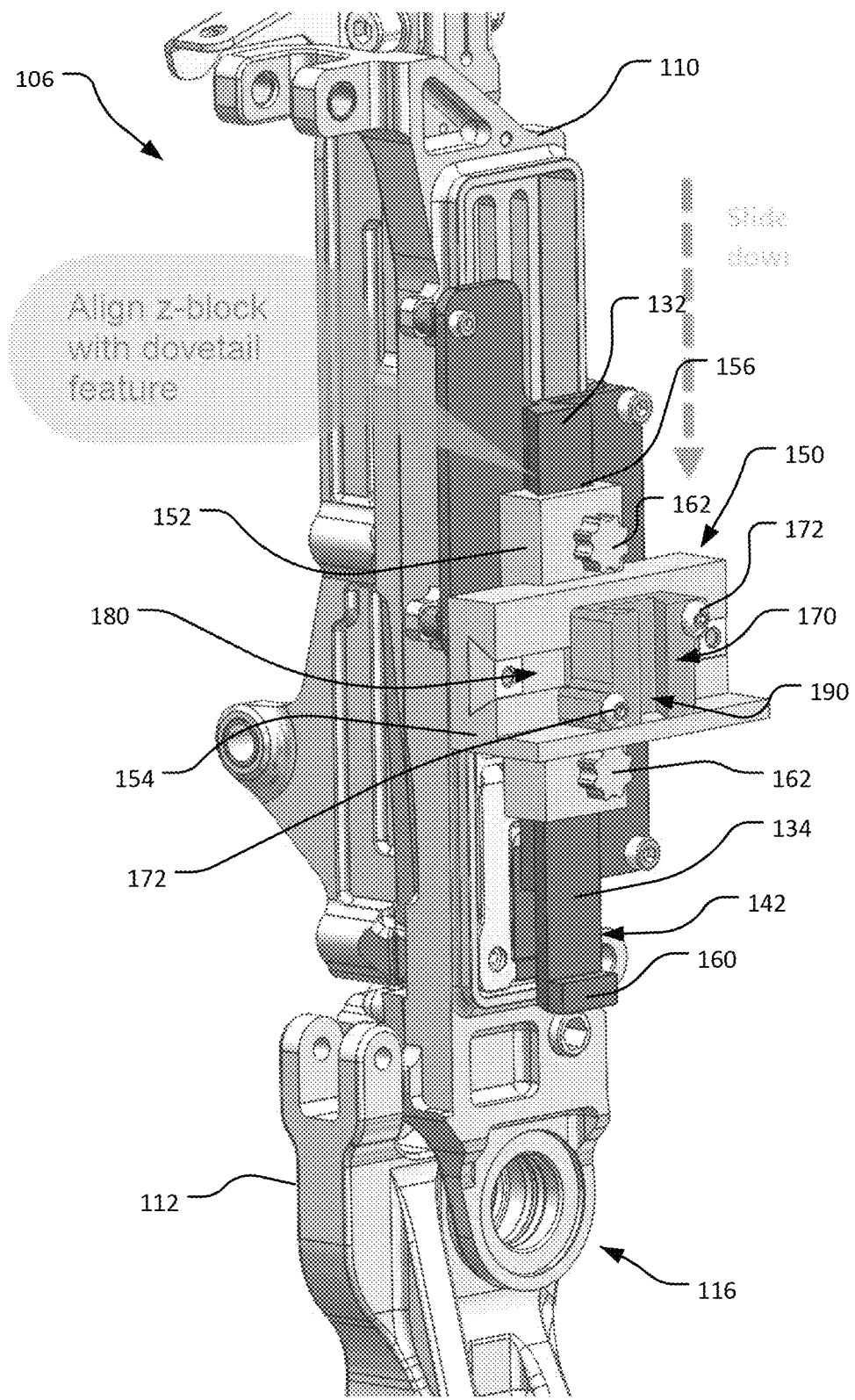
FIG. 4 is similar to FIG. 3, but includes a carrier releasably secured to the upper leg structure.

Referring to FIG. 4, the first carriage portion 150 is of a generally plus-shaped form when viewed front-on and includes a first generally rectangular portion 152 configured to be aligned with the longitudinal axis of the first guide 130 when secured thereto, and a second generally rectangular portion 154 substantially orthogonal to, and forward of, the first rectangular portion 152. The first rectangular portion 152 defines, in a rear face thereof, a first dovetail-shaped recess 156 configured to slidingly interface with the guide surface 142 of the dovetail-shaped rail 132 such that the first carriage portion 150 is slidable along the rail 132 to a desired position (as shown in FIG. 2).

The dovetail-shaped rail 132 includes a rectangular protruding stop 160 at a lower end thereof configured to define a lower limit of sliding travel of the carrier 120 on the rail 132 (a lower end of the first rectangular portion 152 contacting the stop 160 at the lower limit of sliding travel). The first carriage portion 150 is fixable in a desired position along the rail 132 by a pair of manually adjustable fasteners 162 configured to extend though the first rectangular portion 152 of the first carriage portion 150 to engage the rail 132 to secure the first carriage portion 150 at the desired position. A first one of the pair of fasteners 162 extends through the first rectangular portion 152 at a position above the second rectangular portion 154, and a second one of the pair of fasteners 162 extends through the first rectangular portion 152 at a position below the second rectangular portion 154.

The first carriage portion 150 also includes a generally rectangular second carriage portion 170 that is laterally translatable in a transverse channel 180 in a front face of the second rectangular portion 154. The transverse channel 180 is generally orthogonal to a longitudinal axis of the first rectangular portion 152. The laterally translatable second carriage portion 170 is secured in a desired lateral position in the transverse channel 180 by a pair of grub screws 172 located through a front face of the second carriage portion 170 at respective lower-left and upper-right corners.

The second carriage portion 170 defines, in a front face thereof, a second guide in the form of a second generally dovetail-shaped recess 190. A longitudinal axis of the recess 190 is substantially parallel to the longitudinal axis of the first rectangular portion 152, and substantially orthogonal to a longitudinal recess extending through the transverse channel 180.

Figure 5:
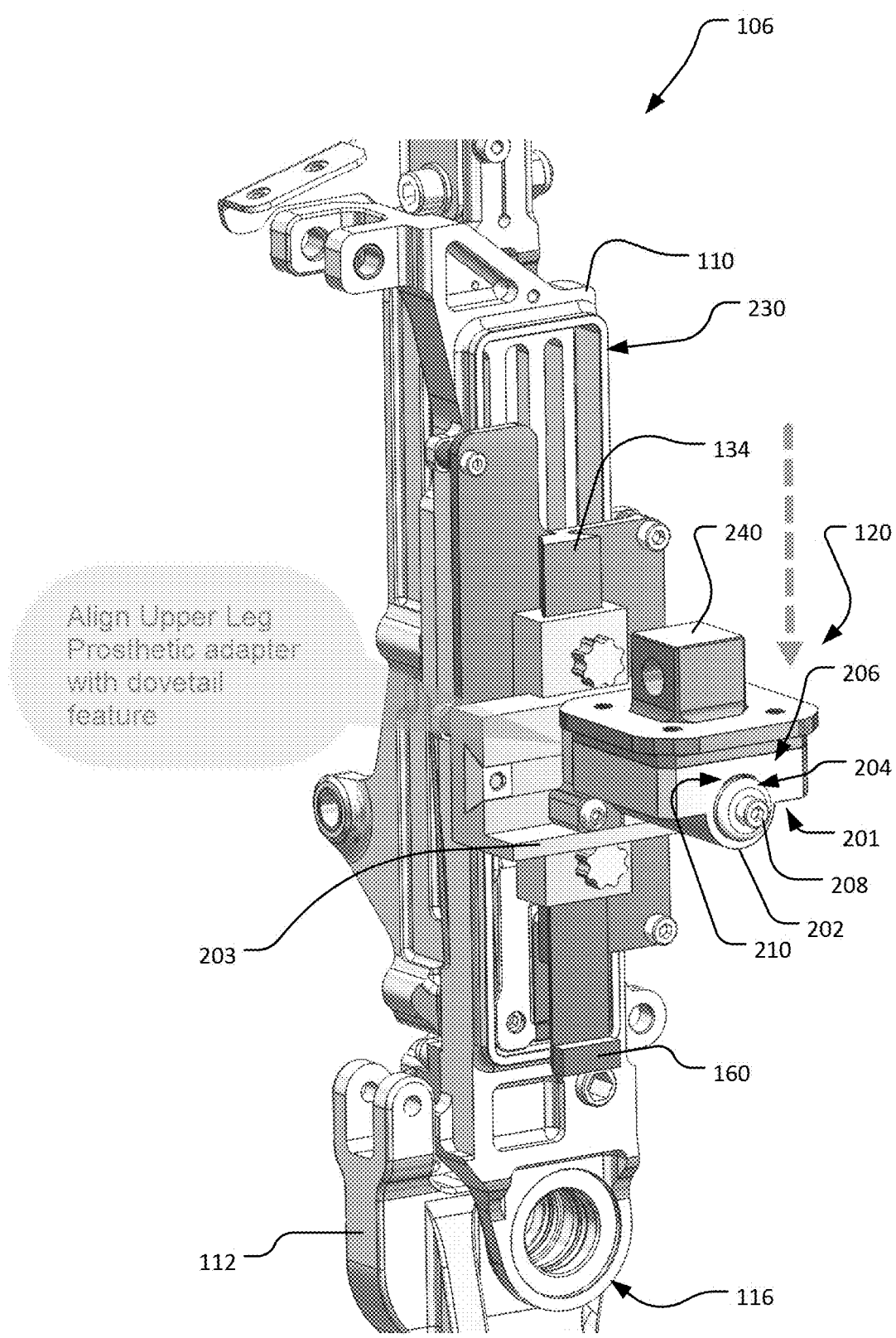
FIG. 5 is similar to FIG. 4, but includes a male Ferrier coupler connected to the carrier.

The dovetail-shaped recess 190 of the second carriage portion 170 is configured to slidingly receive a third carriage portion 201 in the form of a generally rectangular prism with a lower semi-cylindrical protrusion 202 (FIG. 5). A rear face of the third carriage portion 201 includes a dovetail-shaped rail (not shown) that slidingly interfaces with the dovetail-shaped recess 190 of the second carriage portion 170. The third carriage portion 201 is slidable in the dovetail-shaped recess 190 until it is seated against a lower surface 203 (FIG. 5) of the first carriage portion 150. Advantageously, when in this position, the third carriage portion 201 is positionable in at least two perpendicular axes with respect to the upper leg structure 110 (due to the first carriage portion 150 being slidable in a direction parallel to the longitudinal axis of the upper leg structure 110, i.e. in a vertical direction in the saggital plane, and due to the second carriage portion 170 being laterally translatable in the transverse channel 180, i.e. in a horizontal direction in the saggital plane).

The third carriage portion 201 is also configured to be pivotably movable with respect to the second carriage portion 170. To achieve this, the third carriage portion 201 includes a cylindrical recess 204 (FIG. 5) that extends from a front side 206 to a rear side of the third carriage portion 201. Disposed within the recess 204 is a fixed cylindrical pin 208 about which the third carriage portion 201 is pivotably movable. The cylindrical pin 208 defines a pivot axis that is substantially perpendicular the longitudinal axis of the transverse channel 180 and substantially perpendicular to the longitudinal axis of the guide 130, i.e. the pivot axis is normal to the saggital plane. The cylindrical pin 208 includes an upwardly extending radial extension (not shown) that is movable within a similarly shaped radial keyway 210 of the recess 204. The radial keyway 210 defines a range of pivotable movement of the third carriage portion 201. Specifically, the third carriage portion 201 is configured to pivotably move about the fixed cylindrical pin 208 until an inner radial surface of the keyway 210 engages the fixed radial extension of the cylindrical pin 208.

The keyway 210 is dimensioned such that the third carriage portion 201 may pivot about the pivot axis approximately 10° toward anterior and posterior directions. As is typical in above-knee amputations, the remaining part of the upper leg may have a reduced range of motion or may have a generally forward resting position. Therefore, advantageously, the pivotable movement of the third carriage portion 201 may allow for a more comfortable securement of the remaining part of the user's upper leg to the LBE 102.

Figure 6:
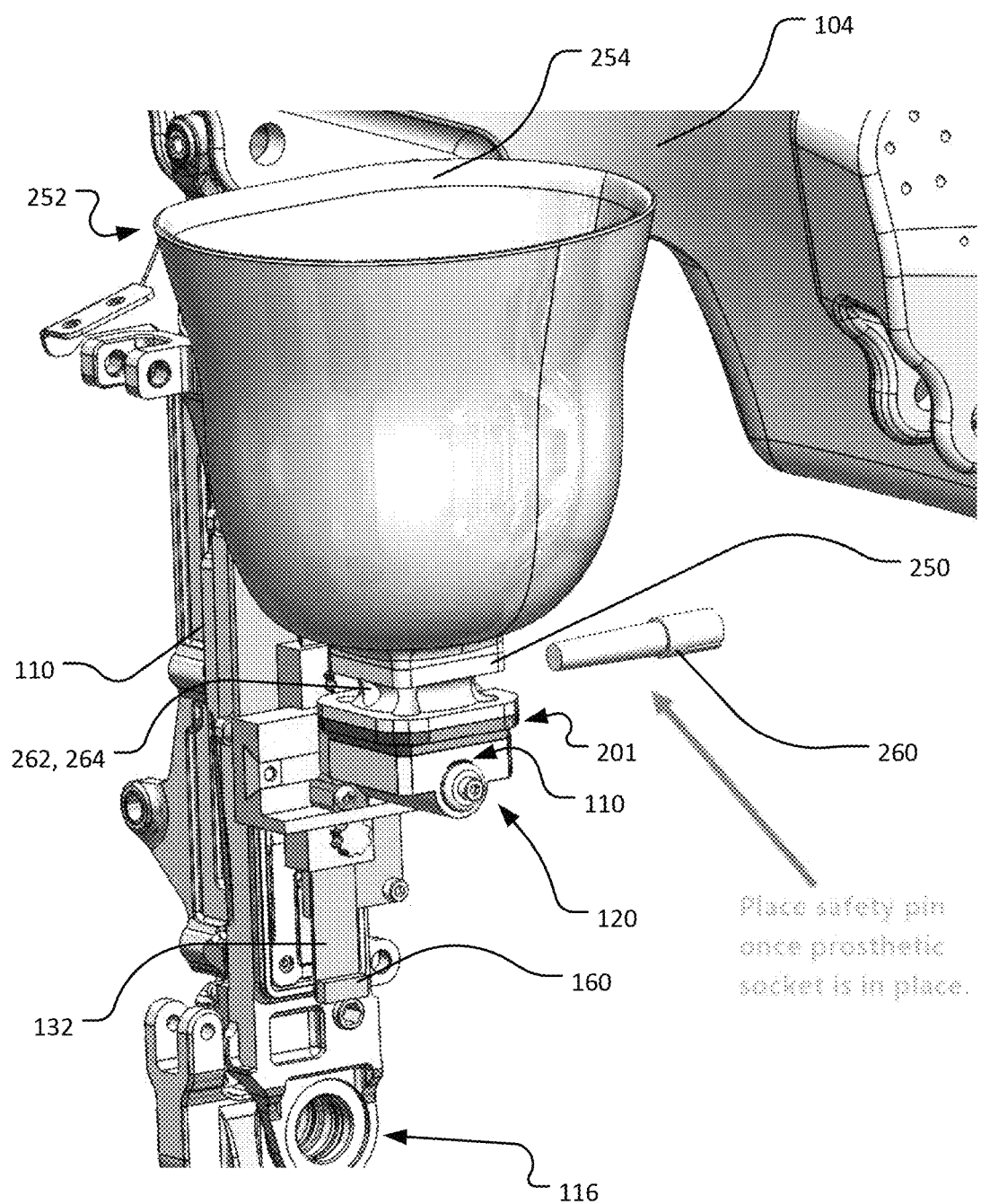
FIG. 6 is similar to FIG. 5, but includes a prosthetic in the form of a socket connected to the male Ferrier coupler.

The third carriage portion 201 also includes a coupling in the form of a male Ferrier coupler 240 on an upper face thereof (FIG. 5). The male Ferrier coupler 240 is configured to mate with a female Ferrier coupler 250 of a prosthetic 252, as shown in FIG. 6. The prosthetic 252 is in the form socket 254 that is shaped like an inverted bell. The socket 254 includes, on an inner surface thereof, a seating surface configured to seat the amputation site of the user, i.e. a stump corresponding to a remaining part of the user's leg after an above-knee amputation.

The prosthetic socket 254 is releasably secured to the carrier 120 by a pin 260 (FIG. 6) that is receivable in respective aligned apertures 262, 264 of the male Ferrier coupler 240 (FIG. 5) and the female Ferrier coupler 240 (FIG. 6).

As is described above, in a first embodiment, the present LBE 102 provides a carrier 120 that is selectively positionable with respect to the upper leg structure 110 of the first and/or second legs 106, 108 of the LBE 102 and which, in use, supports an above-knee amputation site of the user. As is described above, the carrier 120 is selectively positionable with respect to the first and/or second legs 106, 108 in vertical and horizontal directions in the saggital plane, and is pivotable about a pivot axis normal to the saggital plane.

In another embodiment (FIGS. 7 to 10), the LBE 102 may also include another carrier 320 (FIG. 9) that is selectively positionable with respect to the lower leg structure 112 of the first and/or second legs 106, 108 and which, in use, supports a below-knee amputation site of the user.

The carrier 320 includes a mounting arrangement that is substantially similar to the above described mounting arrangement for the carrier 120, and as such, will only be briefly described below.

Figure 7:
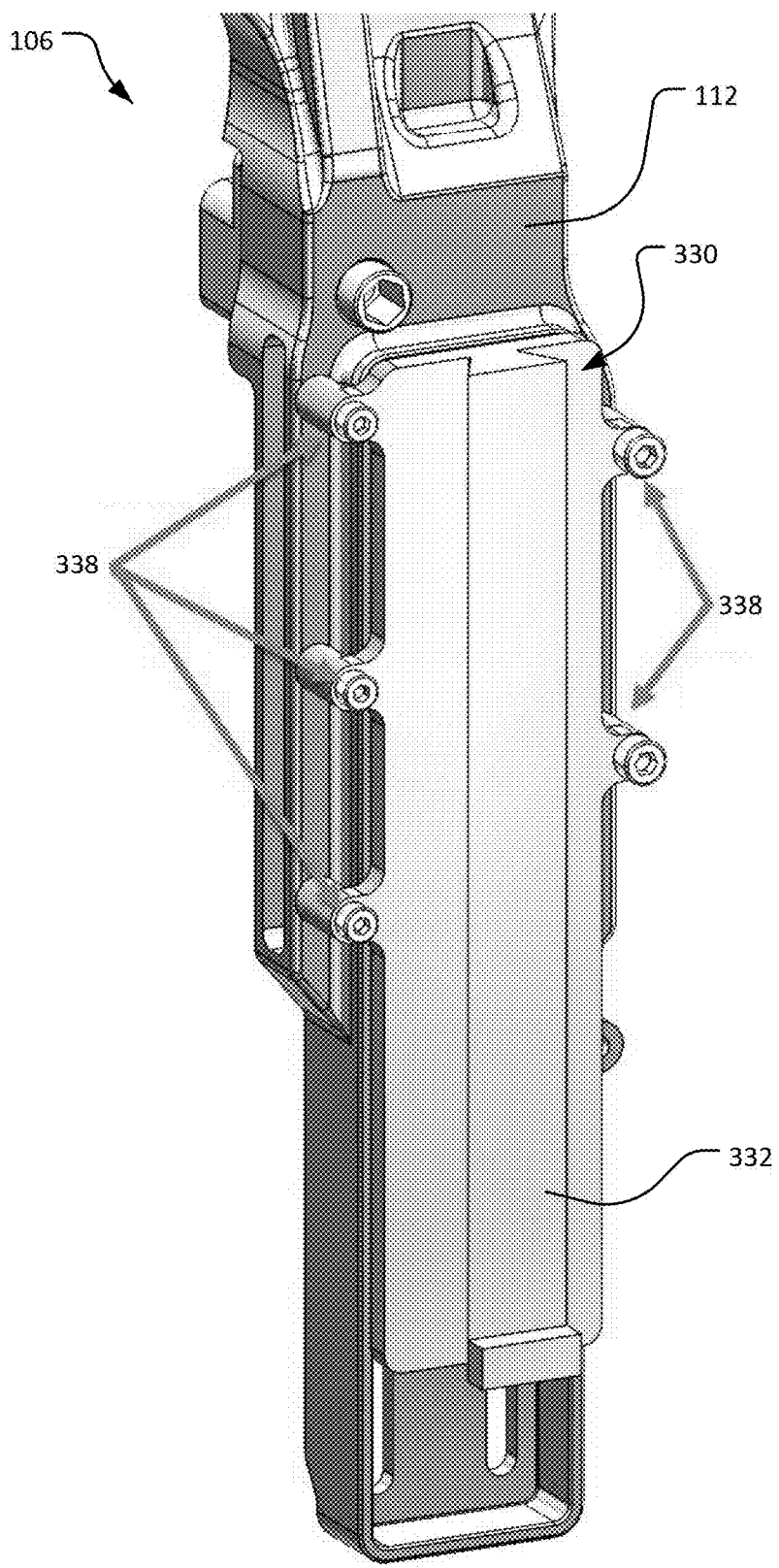
FIG. 7 is a perspective view of a lower leg structure of a single leg of the lower body exoskeleton of FIG. 2.
Figure 8:
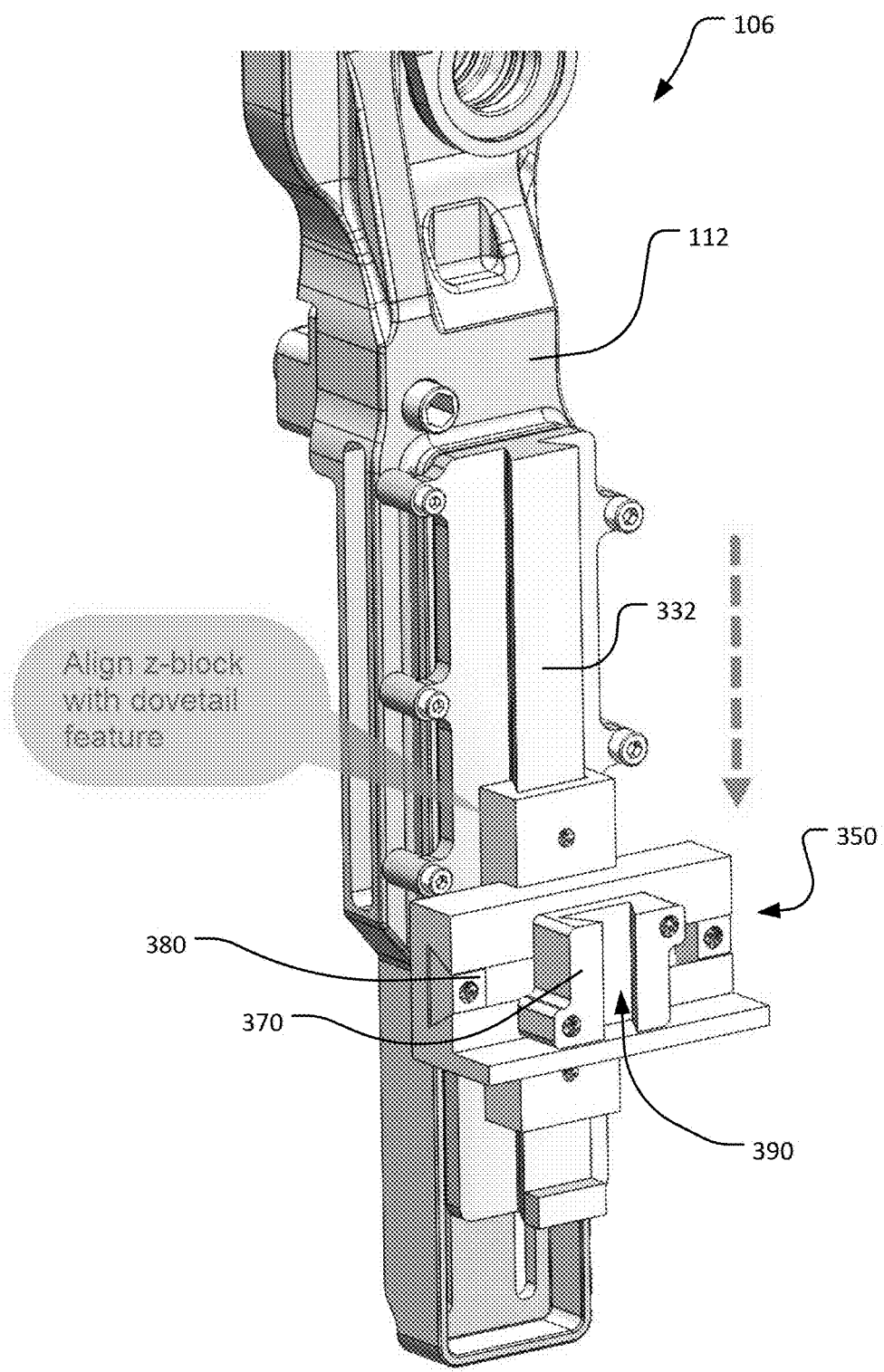
FIG. 8 is similar to FIG. 7, but includes a carrier releasably secured to the lower leg structure.

Referring to FIG. 7, the mounting arrangement includes a generally elongate first guide 330 that is releasably fastenable to the lower leg structure 112 of an inner side surface of the first and/or second legs 106, 108 via fasteners 338. The guide 330 includes a central elongate rail 332 that is dovetail-shaped. Referring to FIG. 8, a generally plus-shaped first carriage portion 350 is slidingly received on the central rail 332 and fixable in a desired position along the central rail 332 in the same manner as described above in relation to the carrier 120. The first carriage portion 350 is substantially similar to the first carriage portion 150. The carrier 320 also includes a second carriage portion 370 that is laterally translatable in a transverse channel 380 of the first carriage portion 350. As such, the carrier 320 is selectively positionable in two perpendicular axes with respect to the lower leg structure 112 (due to the first carriage portion 350 being slidable in a direction parallel to a longitudinal axis of the lower leg structure 110, i.e. in a vertical direction in the saggital plane, and due to the second carriage portion 370 being laterally translatable in the transverse channel 380, i.e. in a horizontal direction in the saggital plane).

Figure 9:
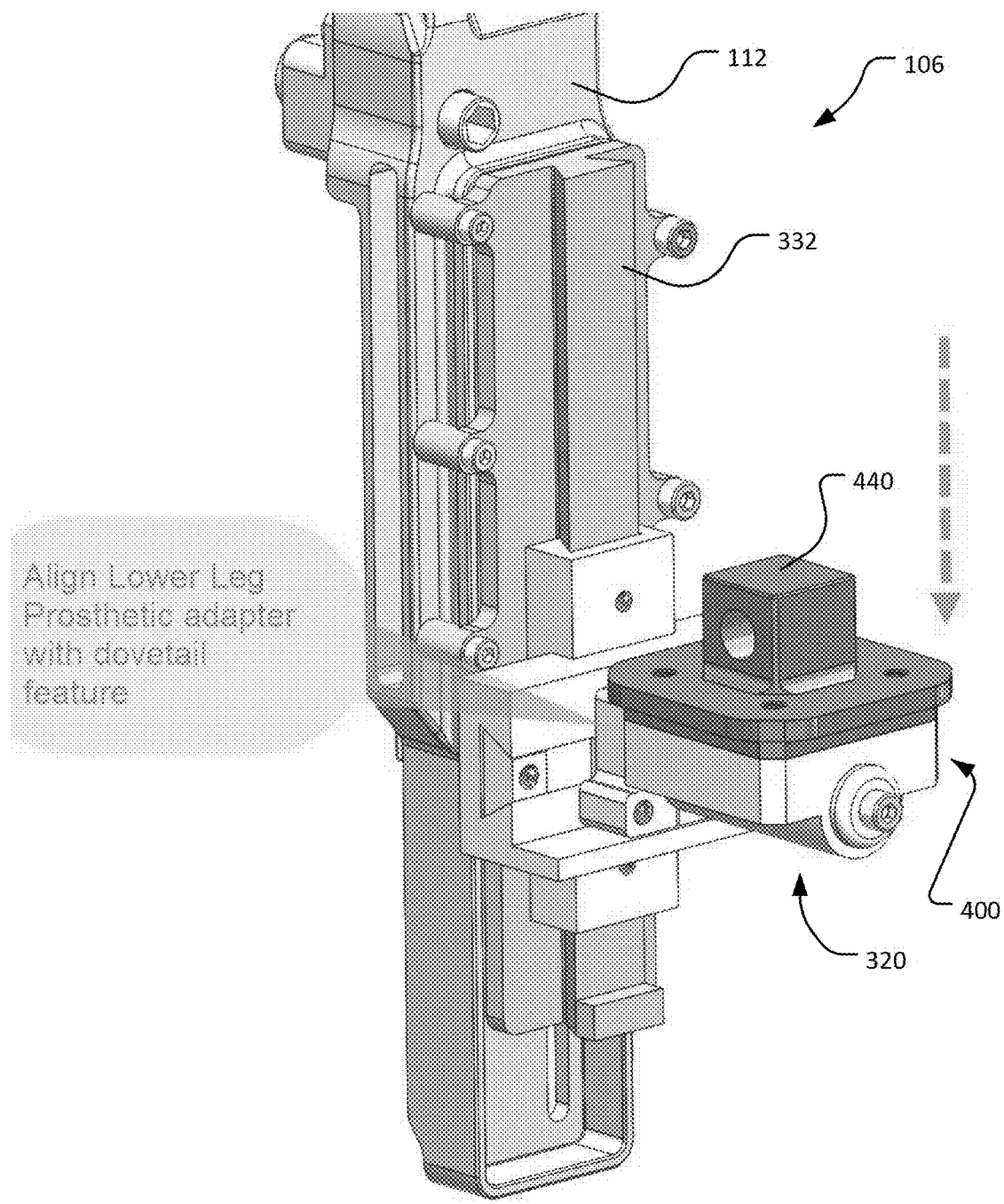
FIG. 9 is similar to FIG. 8, but includes a male Ferrier coupler connected to the carrier.

Referring now to FIG. 9, a third carriage portion 400 includes a coupling in the form of a male Ferrier coupler 440 extending from an upper surface thereof is slidingly received in a second guide in the form of a dovetail-shaped recess 390 (FIG. 8) of the second carriage portion 370. The third carriage portion 400 is substantially similar to the third carriage portion 201, but does not include an inner cylindrical recess (such as recess 204 shown in FIG. 3). As such, the third carriage portion 400 is not pivotably movable with respect to the second carriage portion 370.

Figure 10:
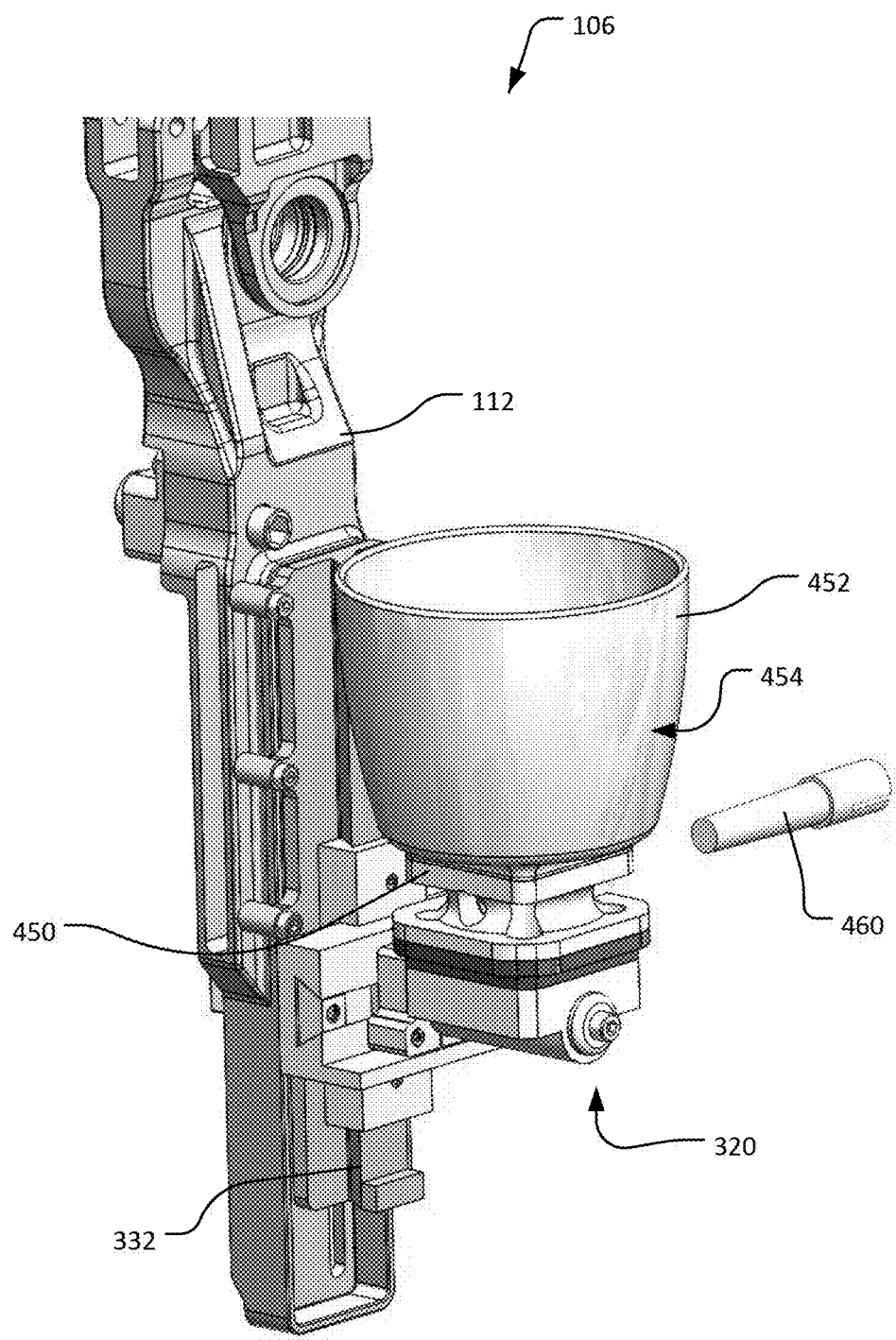
FIG. 10 is similar to FIG. 9, but includes a prosthetic in the form of a socket connected to the male Ferrier coupler.

Referring now to FIG. 10, a prosthetic in the form of a socket 454 shaped like an inverted bell is connected, via a female Ferrier coupler 450 on a lower end thereof, to the male Ferrier coupler 440 by a pin 460 in the same manner as described above in relation to the prosthetic 252. The socket 454 provides a seating surface on an inner surface thereof configured to seat the amputation site of the user, i.e. a stump corresponding to a remaining part of the user's leg after a below-knee amputation.

Accordingly, the LBE 102 may include a carrier 320 that is selectively positionable with respect to the lower leg structure 112 of the first and/or second legs 106, 108 and which, in use, supports a below-knee amputation site of the user. Advantageously, the LBE 102 may be configured to include two carriers 320 (each carrier 320 being mounted to the lower leg structure 112 of each of the first and second legs 106, 108). Alternatively, the LBE 102 may be configured to include a carrier 320 on one of the first and/or second legs 106, 108 to support a below-knee amputation site of the user, and also a carrier 120 on the other of the first and/or second legs to support an above-knee amputation site of the user.

In another embodiment (FIGS. 11 to 13), the LBE 102 includes another carrier 620 (FIG. 12) that is selectively positionable with respect to the pelvic support structure 104 of the LBE 102 in a vertical direction in the saggital plane. The carrier 620 is in the form of a generally oval-shaped platform 622 that is configured to support an amputation site corresponding to a remaining part of the user's pelvis or hips after a double entire leg amputation, or a double high above-knee amputation. Although not illustrated in the figures, the platform 622 may be also be configured to support only a left side or a right side of the user, wherein the left side or the right side includes an amputation site corresponding to an entire leg amputation or a high above-knee amputation. The platform 622 is releasably mounted to the pelvic support structure 104 by a mounting arrangement described below.

Figure 11:
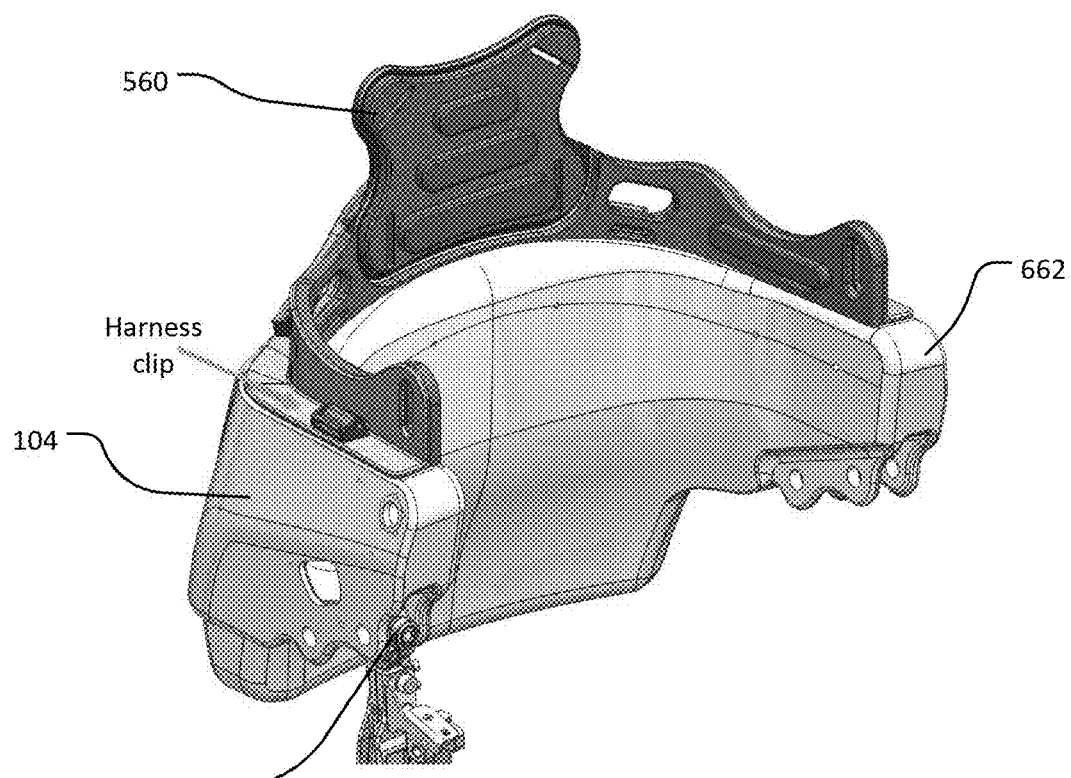
FIG. 11 is a perspective view of a pelvic support structure of the lower body exoskeleton of FIG. 2.

As shown in FIG. 11, a combined back and torso support brace 660 is releasably secured to an upper outer surface 662 of the pelvic support structure 104. The brace 660 may be secured to the pelvic support structure 104 by any means known to those skilled in the art, including by providing double-sided tape on the upper outer surface 662 of the pelvic support structure 104.

Figure 12:
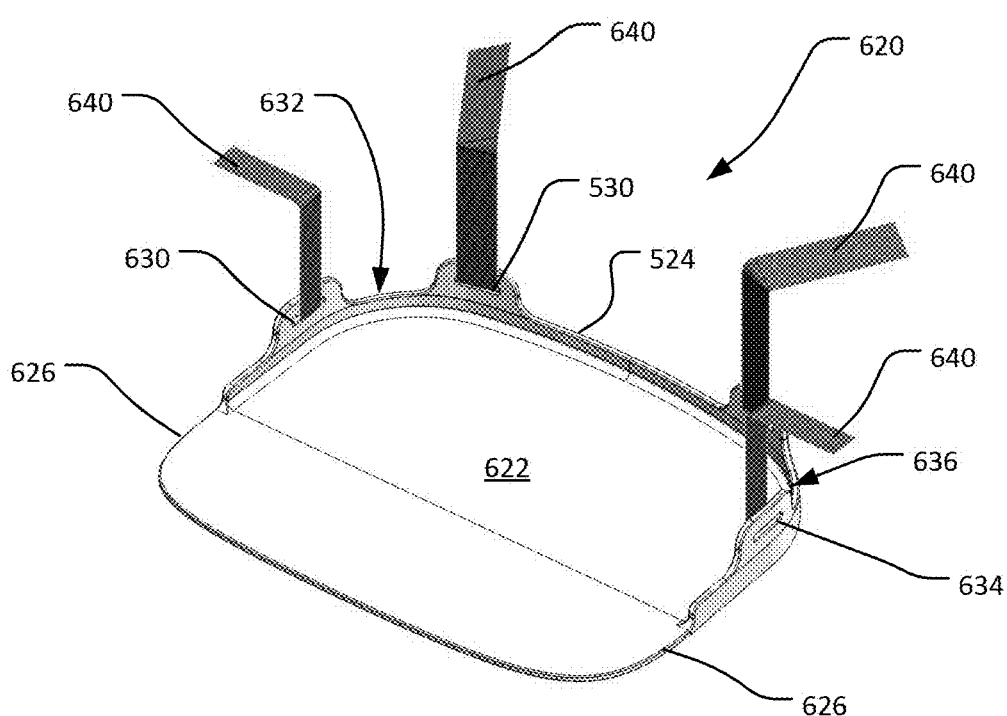
FIG. 12 is a perspective view of an embodiment of a carrier configured to be selectively positioned with respect to the pelvic support structure of FIG. 11.

Referring now to FIG. 12, the platform 622 includes an upstanding wall 624 disposed substantially along a left, a rear, and a right outer side wall 626 of the platform 622. The upstanding wall 624 includes a first pair of apertures 630 located on approximately either side of a left-rear corner 632 of the platform 622, and a second pair of apertures 634 located on approximately either side of right-rear corner 636 of the platform 622. Each of the apertures 630, 634 is dimensioned to receive an elongate strap 640 at a first end of the strap.

Figure 13:
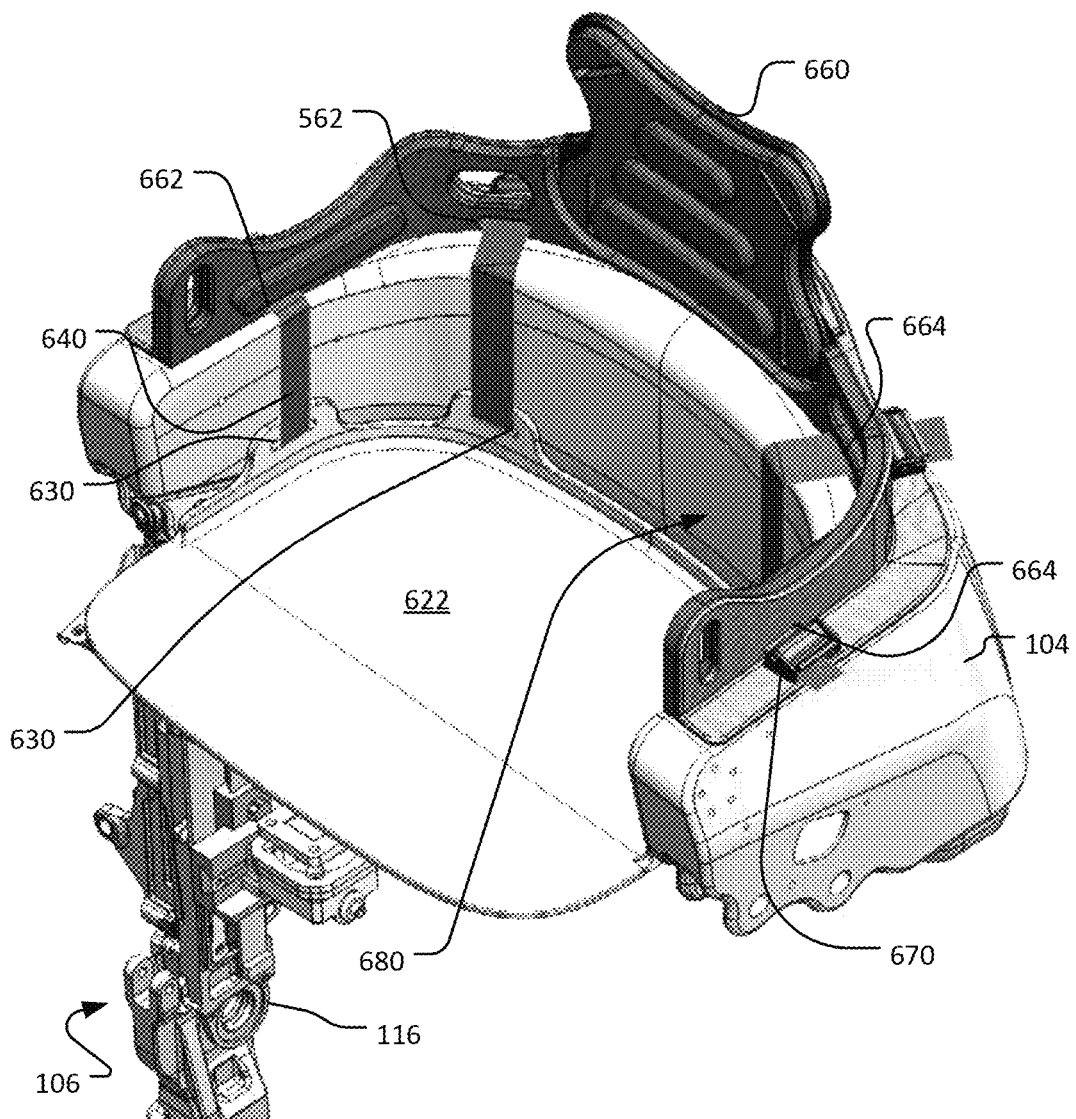
FIG. 13 is a perspective view of the combination of the pelvic support structure of FIG. 11 and the carrier of FIG. 12.

Referring now to FIG. 13, it can be seen that a second opposite end of the each of the straps 540 is received within appropriately dimensioned apertures located within the brace 660. Specifically, the brace 660 includes a first pair of apertures 662 located on approximately either side of a left-rear corner of the pelvic support structure 104, and a second pair of apertures 664 located on approximately either side of a right-rear corner of the pelvic support structure 104. The straps 640 received through the first pair of apertures 630 located in the upstanding wall 624 of the platform 622 are respectively received in the first pair of apertures 662 located within the brace 660. Additionally, the straps 640 received through the second pair of apertures 634 located in the upstanding wall 624 of the platform 622 are respectively received in the second pair of apertures 664 located within the brace 660. The second ends of each of the straps 640 are secured or fixed in clips 670 provided on an outer rear side of the brace 660, as shown in FIG. 13.

As can be seen in FIG. 13, the outer side wall 626 of the platform 622 engages an inner side wall 680 of the pelvic support structure 104 substantially along its entire length when the platform 622 is releasably mounted to the pelvic support structure 104. Furthermore, each of the straps 640 also touch the inner side wall 680 of the pelvic support structure 104 when the platform 622 is releasably mounted thereto. Advantageously, the length of each of the straps 640 between the respective first pairs of apertures 630, 662 and the respective second pairs of apertures 634, 664 may be selectively adjusted such that platform 622 is selectively positionable with respect to the pelvic support structure 104 in the vertical direction in the saggital plane.

As is described above, the present invention provides a LBE 102 suitable for use by a user having amputation site. The LBE 102 may include at least one carrier 120, 320, 620 that, in use, respectively supports an above-knee amputation site, a below-knee amputation site, and an entire-leg or high above-knee amputation site. Any one or more of the carriers 120, 320, and 620 may be utilised with the LBE 102 to support a particular user having one or more corresponding amputation sites. The carrier 120, 320, and 620 and the harness system, in combination, cooperate to position the user, when in use, at a predetermined position relative to the LBE 102. The predetermined position corresponds to a position in which the user's hips (or a remaining part thereof) are located at or approximate to the hip joints 144 (or hip axes) of the LBE 102. As can be seen in FIG. 1, the prior known LBE includes a harness system comprising adjustable waist and leg straps 660 and a series of leg cuffs 691, 692. It is envisaged that the LBE 102 of the present invention would also include similar harness system comprising adjustable waist and leg straps and leg cuffs, and, as is mentioned above, the harness system and carrier would, in combination, cooperate to position the user at the predetermined position with respect to the LBE 102.

In an alternative embodiment of the invention, it is contemplated that the carrier may also include a prosthetic, such as a sockets 254, 454, to receive and seat the amputation site of the user, e.g. the user's stump. In other words, the LBE 102 may be configured to receive and support the amputation site of the user without interfacing with the user's personalised prosthetic. In this embodiment, it is contemplated that the carrier may be have a limited degree of freedom of positioning with respect to the LBE 102. For example, the carrier may be constrained to be selectively positionable in the vertical direction in the saggital plane only.

Although not illustrated in the figures, the first and second legs 106, 108 are length adjustable to suit the user. The upper and lower leg structures 110, 112 of each of the first and second legs 106, 108 includes at least two leg members that are selectively positionable with respect to each other. Accordingly, both the upper leg structure 110 and the lower leg structure 112 of each of the first and second legs 106, 108 are length adjustable. Advantageously therefore, the LBE 102 provides a double adjustability arrangement whereby the first and second legs 106, 108 are length adjustable to suit the user, and in addition, the position of the carrier 120, 320, and 620 is also adjustable to suit the amputation site of the user. This double adjustability, in combination with the harness system, allows the user to be positioned at the predetermined position mentioned above.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A mobility aid for use by a user having a lower body amputation site, the mobility aid including:
   a lower body exoskeleton being a free-standing electromechanical skeletal structure configured to be worn externally by the user and configurable to be fully supportive of the user, including:
   a pelvic support structure;
   a first leg and a second leg, each of the first and second legs movably coupled to the pelvic support structure, wherein at least the first and second legs are selectively actuable to move the lower body exoskeleton relative to a surface on which the mobility aid is positioned, wherein at least one of the first leg or the second leg includes a first guide that includes one or more rails;
   a carrier selectively positionable with respect to the lower body exoskeleton and, which in use, supports the user at or about an amputation site, wherein the first guide is adapted to receive and retain the carrier; and
   a harness system configured to, when in use, secure the user to the lower body exoskeleton;
   wherein the carrier includes:
     a first carriage portion configured to slidingly interface with the one or more rails of the first guide such that the carrier is slidable along the first guide and such that the carrier can be selectively positionable and releasably secured along the first guide in a first direction in a sagittal plane;
     a second carriage portion configured to be mounted to the first carriage portion and being laterally translatable on the first carriage portion, the second carriage portion including a second guide; and
     a third carriage portion slidingly receivable by the second guide, the third carriage portion being selectively positionable in a second direction in the sagittal plane, said second direction being perpendicular to the first direction, thereby the carrier being selectively positionable in at least two perpendicular axes in the sagittal plane.

2. The mobility aid as claimed in claim 1 wherein the carrier is a first carrier and the lower body exoskeleton includes a second carrier selectively positionable with respect to the lower body exoskeleton, wherein said second carrier is arranged to support the user at or about a second amputation site.

3. The mobility aid as claimed in claim 1 wherein the first and second legs are pivotally coupled to the pelvic support structure at respective first and second hip joints, each of the first and second hip joints defining respective first and second hip axes about which the legs have a rotational degree of freedom, wherein one or more of the carrier and the harness system, in combination, cooperate to position the user, when in use, such that at least one of the user's hips is located at or proximate to at least one of said first and second hip axes.

4. The mobility aid as claimed in claim 1 wherein the first direction is a vertical direction in the sagittal plane.

5. The mobility aid as claimed in claim 1 wherein the second direction is a horizontal direction in the sagittal plane.

6. The mobility aid as claimed in claim 1 wherein the carrier is pivotable about a pivot axis substantially normal to the sagittal plane.

7. The mobility aid as claimed in claim 1 wherein the third carriage portion is pivotably movable with respect to the second carriage portion.

8. The mobility aid as claimed in claim 1 wherein the carrier includes a coupling to couple the carrier with a prosthetic.

9. The mobility aid as claimed in claim 8 wherein the coupling is a part of a Ferrier coupler.

10. The mobility aid as claimed in claim 1, further including a second carrier releasably mounted to the pelvic support structure such that said second carrier is selectively positionable with respect to the pelvic support structure in a vertical direction in the sagittal plane, said carrier including a platform that defines a seating surface configured to support an amputation site of the user.

11. The mobility aid as claimed in claim 1 wherein the harness system of the lower body exoskeleton includes any one or more of:
    braces, tethers, strapping, a harness, or webbing to hold the user's hips to the pelvic support structure;
    adjustable straps or webbing that extend about the torso and/or at least one limb or a remaining part of at least one limb of the user; and
    an orthotics system configured to interface with and secure, if present, at least one foot of the user to the lower body exoskeleton.

12. The mobility aid as claimed in claim 1 wherein the first and second legs are length adjustable, and each leg includes an upper and a lower leg structure, each of which includes at least two leg members that are selectively positionable with respect to each other.

13. The mobility aid as claimed in claim 1 wherein both the first leg and the second leg include respective first guides each including one or more rails, each respective first guide being adapted to receive and retain respective carriers.

14. The mobility aid as claimed in claim 1, wherein the first guide includes a stop at one end thereof to define a limit of sliding travel of the carrier on the first guide.

15. The mobility aid as claimed in claim 1, the first carriage portion includes a first recess that slidingly interfaces with the one or more rails of the first guide such that the carrier is slidable along the first guide.

16. The mobility aid as claimed in claim 1, wherein the carrier is securable along the first guide at the desired position by one or more fasteners that are received through the first carriage portion to engage the first guide.

* * * * *